US012624339B2

(12) United States Patent
Chen et al.

(10) Patent No.: US 12,624,339 B2
(45) Date of Patent: May 12, 2026

(54) BRAIN ORGANOID CONTAINING OPTIC VESICLES GENERATED BASED ON H9 INDUCTION AND EYE-BRAIN FUSION CULTURE METHOD

(71) Applicant: Tianjin University, Tianjin (CN)

(72) Inventors: Liqun Chen, Tianjin (CN); Rui Hu, Tianjin (CN); Dong Ming, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 19/227,561

(22) Filed: Jun. 4, 2025

(65) Prior Publication Data

US 2025/0297213 A1     Sep. 25, 2025

Related U.S. Application Data

(63) Continuation of application No. PCT/CN2025/084058, filed on Mar. 21, 2025.

(30) Foreign Application Priority Data

Jan. 29, 2024   (CN) ........................ 202410121193.X

(51) Int. Cl.
    *C12N 5/079*      (2010.01)
    *C12N 5/00*      (2006.01)

(52) U.S. Cl.
    CPC ......... *C12N 5/0618* (2013.01); *C12N 5/0062* (2013.01); *C12N 2500/38* (2013.01); *C12N 2501/13* (2013.01); *C12N 2501/155* (2013.01); *C12N 2506/02* (2013.01); *C12N 2509/00* (2013.01); *C12N 2513/00* (2013.01); *C12N 2533/90* (2013.01)

(58) Field of Classification Search
None
See application file for complete search history.

(56) References Cited

FOREIGN PATENT DOCUMENTS

| | | |
|---|---|---|
| CN | 116376840 A | 7/2023 |
| CN | 117286106 A | 12/2023 |

OTHER PUBLICATIONS

Gabriel, Elke, et al. "Human brain organoids assemble functionally integrated bilateral optic vesicles." Cell stem cell 28.10 (2021): 1740-1757. (Year: 2021).*
Notice of first Office action dated Dec. 20, 2024 in SIPO application No. 202410121193.X, 18 pages.
Retrieval report-First search dated Dec. 18, 2024 in SIPO application No. 202410121193.X, 6 pages.
Notification to Grant Patent Right for Invention dated Feb. 7, 2025 in SIPO application No. 202410121193.X, 3 pages.
Retrieval report—Supplementary search dated Jan. 27, 2025 in SIPO application No. 202410121193.X, 4 pages.
Shujin Chen et al., "Proteome signatures of joint toxicity to arsenic (As) and lead (Pb) in human brain organoids with optic vesicles", Environmental Research, Dec. 8, 2023, Section 2.1-2.4, Figure 1, Lines 41-101 of Supplementary Information, Table S1, vol. 243, 27 pages.
Elke Gabriel et al., 'Human brain organoids assemble functionally integrated bilateral optic vesicles', Cell Stem Cell, Oct. 7, 2021, pp. e3-e4, vol. 28, 27 pages.

* cited by examiner

*Primary Examiner* — Peter Paras, Jr.
*Assistant Examiner* — Constantina E Stavrou
(74) *Attorney, Agent, or Firm* — COOPER LEGAL GROUP LLC

(57) ABSTRACT

A brain organoid containing optic vesicles generated based on H9 induction and an eye-brain fusion culture method thereof are provided. H9 embryonic stem cell induction is used to generate a brain organoid containing optic vesicles with primitive visual field. Based on an established optic vesicle brain organoid culture system, microscopic imaging is combined with specific marker antibodies related to early retinal development and photoreceptor cell maturation to structurally and functionally identify the brain organoid containing optic vesicles.

1 Claim, 13 Drawing Sheets

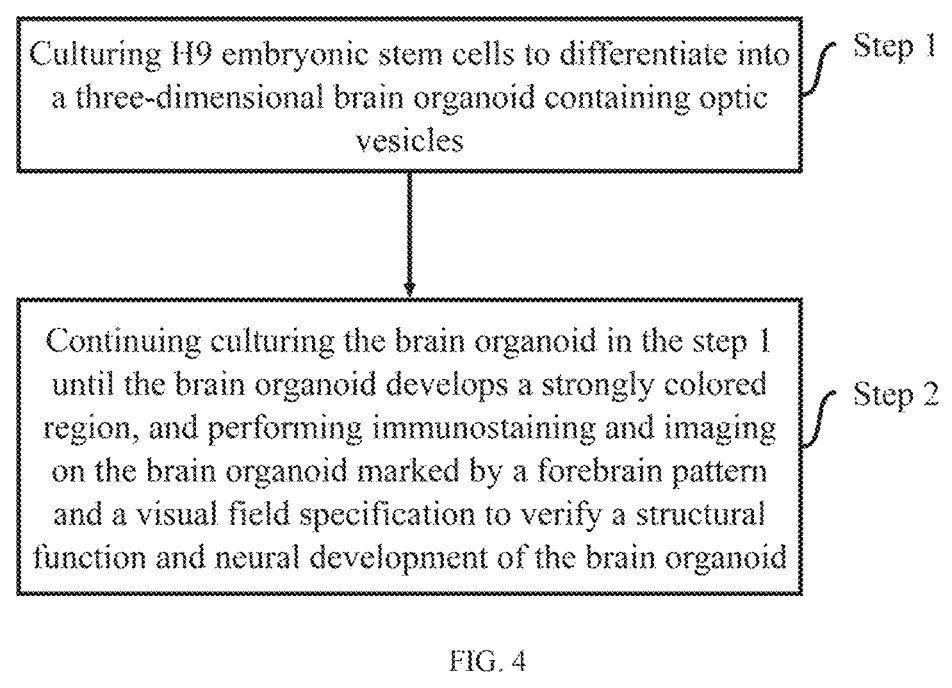

Culturing H9 embryonic stem cells to differentiate into a three-dimensional brain organoid containing optic vesicles — Step 1

Continuing culturing the brain organoid in the step 1 until the brain organoid develops a strongly colored region, and performing immunostaining and imaging on the brain organoid marked by a forebrain pattern and a visual field specification to verify a structural function and neural development of the brain organoid — Step 2

FIG. 4

BRAIN ORGANOID CONTAINING OPTIC VESICLES GENERATED BASED ON H9 INDUCTION AND EYE-BRAIN FUSION CULTURE METHOD

CROSS-REFERENCE TO RELATED APPLICATIONS

This application is a continuation of PCT/CN2025/084058, filed Mar. 21, 2025, which claims priority of Chinese Patent Application No. 202410121193.X, filed on Jan. 29, 2024. The entire contents of International Patent Application PCT/CN2025/084058 and Chinese Patent Application No. 202410121193.X are incorporated herein by reference.

TECHNICAL FIELD

The present disclosure relates to the field of biomedical technology, and in particular relates to a brain organoid containing optic vesicles generated based on H9 induction and an eye-brain fusion culture method.

BACKGROUND

Human brain organoids are miniature brains cultured in a culture medium that simulates the brain developmental environment using induced pluripotent stem cells (iPSCs). Human brain organoids exhibit cellular and structural characteristics of the human brain and may replicate fetal brain development pathways, providing excellent models for studying development, diseases, and medicine efficacy, and offering unprecedented opportunities for brain organoid transplantation for the treatment of neurological diseases. Retinal organoids (ROs) are cell aggregates formed by the differentiation of embryonic stem cells and induced pluripotent stem cells through specific culture, with a structure and function similar to the corresponding retinal tissue. First reported in 2012, subsequent studies after 2014 have shown that retinal organoid transplants may be used to treat retinitis pigmentosa, retinal epithelial dysfunction, and age-related macular degeneration, improving visual function. During normal embryonic development, the retinal primordium originates from the diencephalon on both sides of the forebrain. A bilayer cup-shaped structure is formed during the development of the eye embryo, which develops forward from the optic disc and eventually develops into the retina. This structure may perceive light and transmit signals to other brain regions. Therefore, constructing a culture for generating optic vesicles based on human brain organoid induction holds significant research value.

Optic vesicle brain organoids have broad applications in biology and medicine. In retinal development, observing and analyzing the developmental process of pluripotent stem cell induced development of optic vesicle brain organoids may enhance understanding of retinal tissue formation and developmental mechanisms. The eye-brain fusion culture mechanism enables retinal ganglion cells to form extensive axonal projections in the forebrain region, opening new avenues for in vitro studies of human embryonic brain and eye development within a single organoid. In terms of disease modeling, optic vesicle brain organoids may be used to establish disease-related models for studying the etiology and pathogenesis of retinal disorders. In terms of medicine screening and evaluation, researchers may assess the therapeutic effects and safety of medicines on retinal diseases by studying the effects of medicines on the optic vesicle brain organoids, providing new ideas and methods for medicine development. In terms of environmental toxicology, such optic vesicle brain organoids may also be used as models to analyze the effects of the environment on embryonic brain and eye development, such as atmospheric pollutants, soil pollutants, water pollutants, radiation pollution, pesticide pollution, viruses, etc. In the field of regenerative medicine, optic vesicle brain organoids also provide marker cells related to retinal organs (such as retinal progenitor cells, optic ganglion cells, retinal pigment epithelial cells, amacrine cells, photoreceptor precursor cells, visual restorative proteins, etc.), which may be used to explore and promote the repair and regeneration ability of damaged retinal tissue. In summary, optic vesicle brain organoids represent a technology with wide-ranging applications, offering new insights and methods for the study and treatment of visual system-related diseases. However, research on the culture for generating optic vesicles of brain organoids based on H9 induction has not yet been reported.

SUMMARY

To address the shortcomings of the aforementioned technical solutions, an objective of the present disclosure is to provide an eye-brain fusion culture method for generating a brain organoid containing optic vesicles based on H9 induction.

Another objective of the present disclosure is to provide a brain organoid containing optic vesicles obtained through the aforementioned culture method.

The objectives of the present disclosure are achieved through the following technical solutions.

An eye-brain fusion culture method for generating a brain organoid containing optic vesicles based on H9 induction includes the following steps:

step 1, culturing H9 embryonic stem cells to differentiate into a three-dimensional brain organoid containing optic vesicle, including following steps:

culturing the H9 embryonic stem cells in an MTESR™ 1 medium (a feeder-free culture and maintenance medium for human embryonic stem cells and induced pluripotent stem cells) until a cell confluence reaches 70%, preparing a single cell suspension, adding a neural induction medium containing 10 mole per liter (mM) Y27632, inoculating in an orifice plate, changing half of the medium with a neural induction medium without 10 mM Y27632 every day, culturing for 0-5 days, forming neurospheres, adding a neurosphere medium, and standing for culture; changing half of the medium with the neurosphere medium every day, culturing until the 6th-7th day, adding an early-stage optic vesicle brain organoid medium on the 8th day, adding a mature-stage optic vesicle brain organoid medium on the 10th day for rotational culture, and changing half of the medium with the mature-stage optic vesicle brain organoid medium every week until the three-dimensional brain organoid containing optic vesicles is differentiated; and step 2, continuing culturing the brain organoid in the step 1 until the brain organoid develops a strongly colored region, and performing immunostaining and imaging on the brain organoid marked by a forebrain pattern and a visual field specification to verify a structural function and neural development of the brain organoid.

In the step 1, the neural induction medium includes 83% Dulbecco's modified eagle medium/nutrient mixture F-12 (DMEM/F-12), 15% KNOCKOUT™ serum replacement (serum replacement supplement), 1% MEM-non-essential amino acids (MEM-NEAA), 1% GLUTAMAX® supplement (L-alanyl-L-glutamine dipeptide supplement), 50 micromolar (μM) β-mercaptoethanol, 10 μM SB431542, and 2 μM XAV939.

In the step 1, the neurosphere medium includes 48% DMEM/F-12, 48% NEUROBASAL™ medium (neuronal cell culture medium), 0.4% N2 supplement, 1% B27 supplement without vitamin A, 0.5% MEM-NEAA, 1% GLUTA-MAX® supplement (L-alanyl-L-glutamine dipeptide supplement), 1% penicillin/streptomycin, 50 μM β-mercaptoethanol, 2.5 μM SB431542, 1.5 nanomolar (nM) bone morphogenetic protein-4 (BMP-4), and 0.1% MATRIGEL® (extracellular matrix).

In the step 1, the early-stage optic vesicle organoid medium includes 48% DMEM/F-12, 48% NEUROBASAL™ medium (neuronal cell culture medium), 0.4% $N_2$ supplement, 1% B27 supplement, 100 nanomole (nMol) retinol acetate, 0.5% MEM-NEAA, 1% GLUTA-MAX® supplement (L-alanyl-L-glutamine dipeptide supplement), 0.5 μM Dorsomorphin, 1% penicillin-streptomycin, 50 μM β-mercaptoethanol, 2.5 μM SB431542, 1.5 μM BMP-4, and 0.1% MATRIGEL® (extracellular matrix).

In the step 1, the mature-stage optic vesicle brain organoid medium includes 48% DMEM/F-12, 48% NEUROBASAL™ medium (neuronal cell culture medium), 0.4% N2 supplement, 1% B27 supplement, 100 nMol retinol acetate, 0.5% MEM-NEAA, 1% GLUTAMAX® supplement (L-alanyl-L-glutamine dipeptide supplement), 0.5 μM Dorsomorphin, 1% penicillin-streptomycin, 50 μM β-mercaptoethanol, 2.5 μM SB431542, 0.1% Ascorbic acid, 10 nanogram per milliliter (ng/ml) brain-derived neurotrophic factor (BDNF), and 10 ng/ml ciliary neurotrophic factor (CNTF).

The brain organoid containing optic vesicles obtained through the aforementioned culture method.

The advantages and beneficial effects of the present disclosure are as follows.

The present disclosure utilizes H9 embryonic stem cell induction to generate a brain organoid containing optic vesicles with primitive visual field. Based on an established optic vesicle brain organoid culture system, microscopic imaging is combined with specific marker antibodies related to early retinal development and photoreceptor cell development and maturation to structurally and functionally identify the brain organoid containing optic vesicles.

The present disclosure innovatively integrates retinal structures with brain organoids, facilitating research on interactions between the retina and forebrain, providing an in vitro model for studying brain and eye development and diseases, and offering a new approach for investigating the effects of medicines and environmental exposures on human embryonic brain and eye development.

BRIEF DESCRIPTION OF THE DRAWINGS

FIG. 4 is a flowchart of an eye-brain fusion culture method for generating a brain organoid containing optic vesicles based on H9 induction according to the present disclosure.

DETAILED DESCRIPTION OF THE EMBODIMENTS

The technical solutions of the present disclosure are further described below with reference to specific embodiments.

Embodiment 1

Figure 1A:
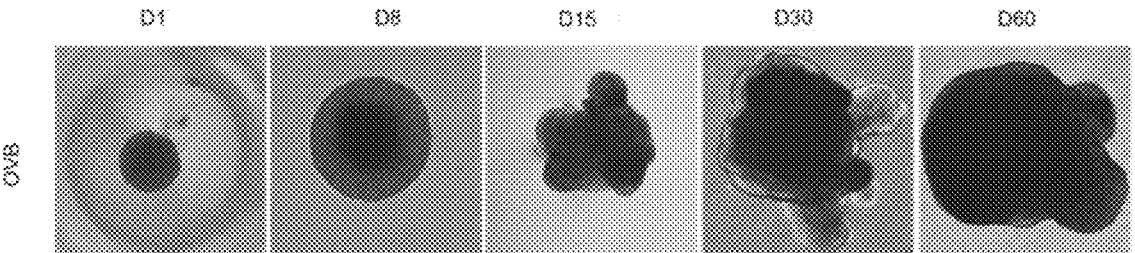
FIG. 1A shows light microscope images of a brain organoid containing optic vesicles.
Figure 1B:
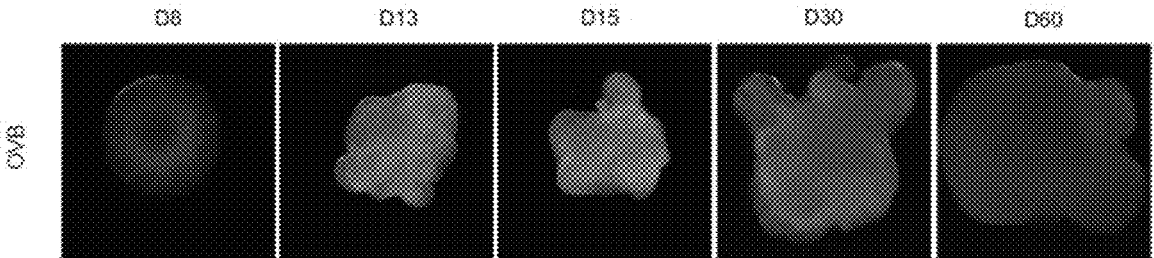
FIG. 1B shows light microscope images of the brain organoid containing optic vesicles.
Figure 2A:
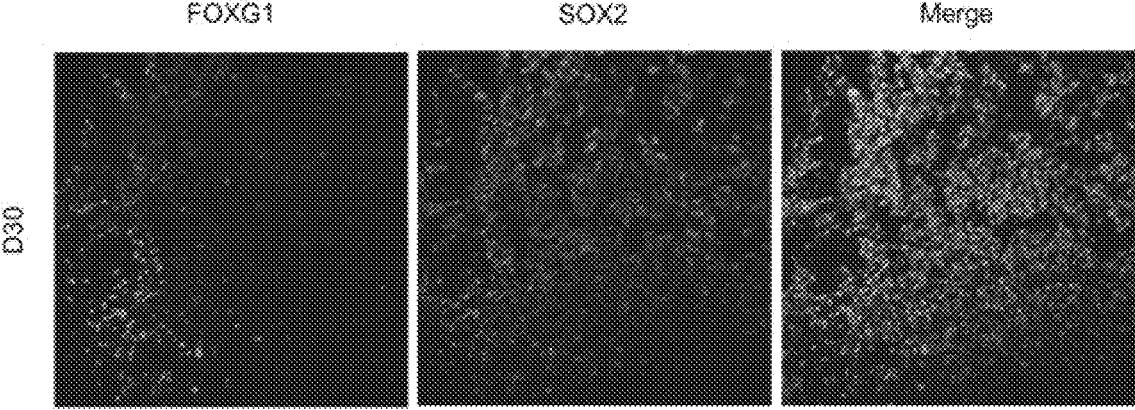
FIG. 2A shows immunofluorescence of forebrain patterning molecules Forkhead Box G1 (FOXG1) and neural progenitor cells Sex Determining Region Y Box 2 (SOX2).
Figure 2B:
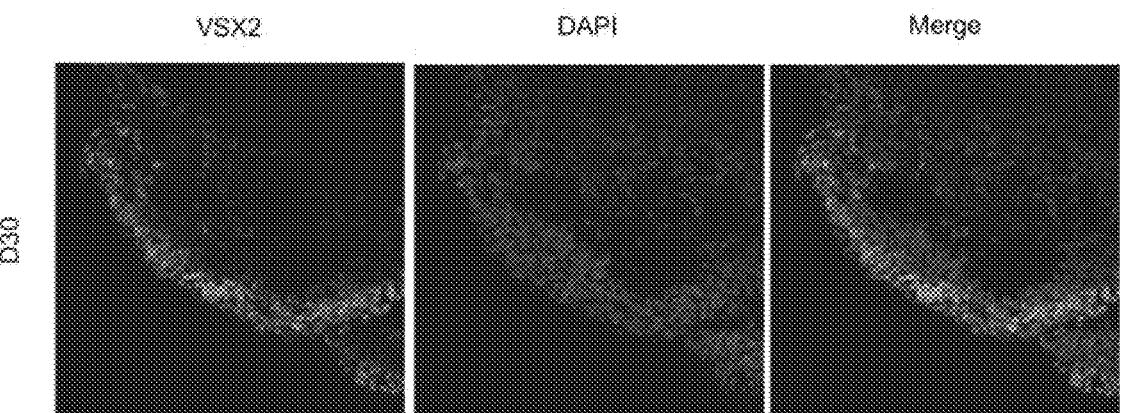
FIG. 2B shows immunofluorescence of retinal progenitor cells visual system homeobox 2 (VSX2).
Figure 3A:
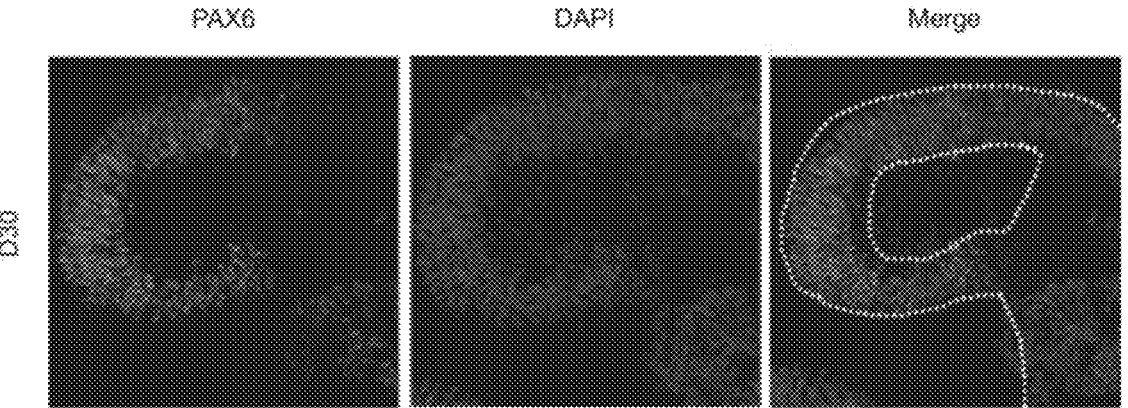
FIG. 3A shows immunofluorescence of optic progenitor cells paired box gene 6 (PAX6).
Figure 3B:
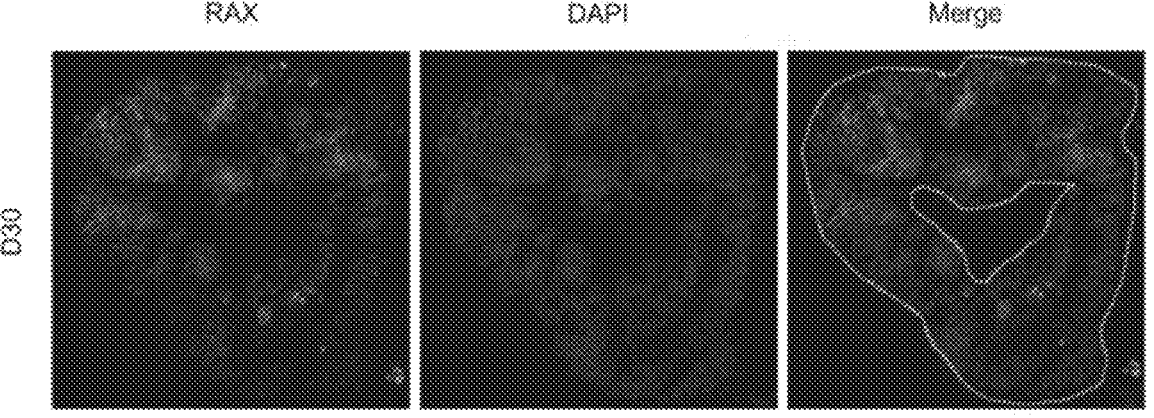
FIG. 3B shows immunofluorescence of primitive visual field region molecules determining photoreceptor fate retina and anterior neural fold homeobox (RAX).
Figure 3C:
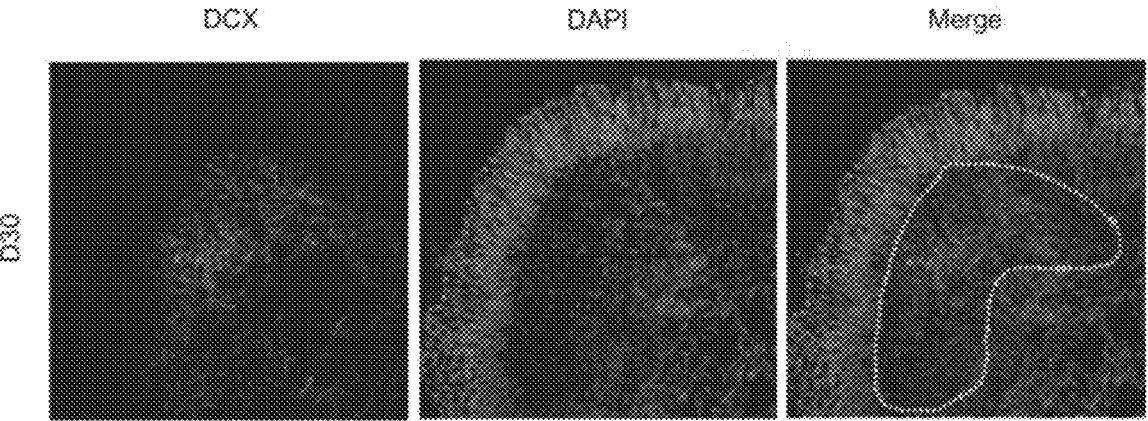
FIG. 3C shows immunofluorescence of neuronal precursor cells doublecortin (DCX).
Figure 3D:
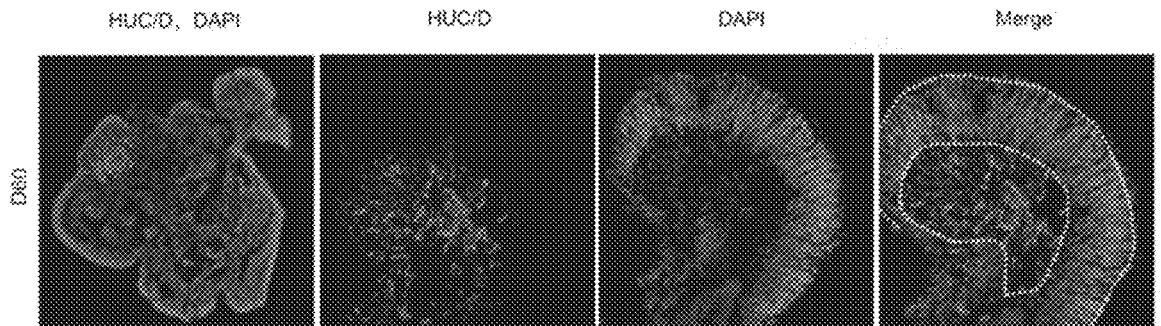
FIG. 3D shows immunofluorescence of amacrine cells HUC/D.
Figure 3E:
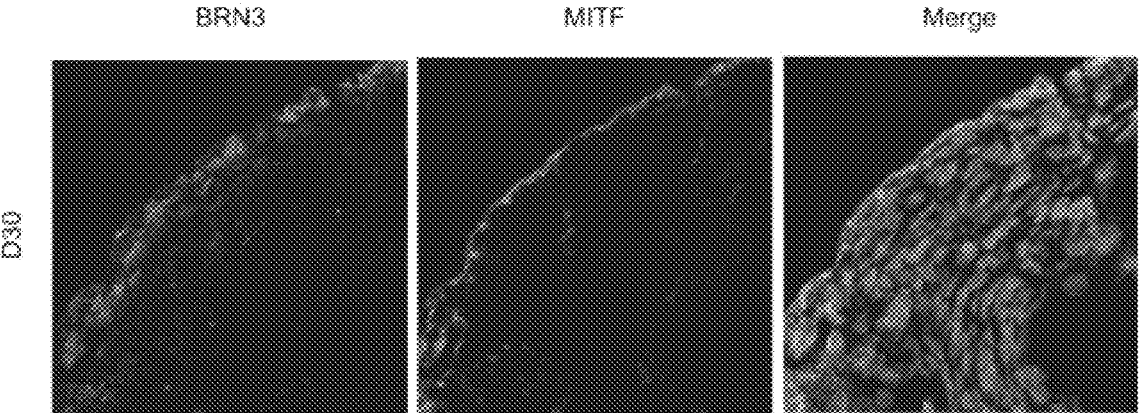
FIG. 3E shows immunofluorescence of optic ganglion cells brain-specific homeobox/POU domain protein 3 (BRN3) and retinal epithelial cells microphthalmia-associated transcription factor (MITF).
Figure 3F:
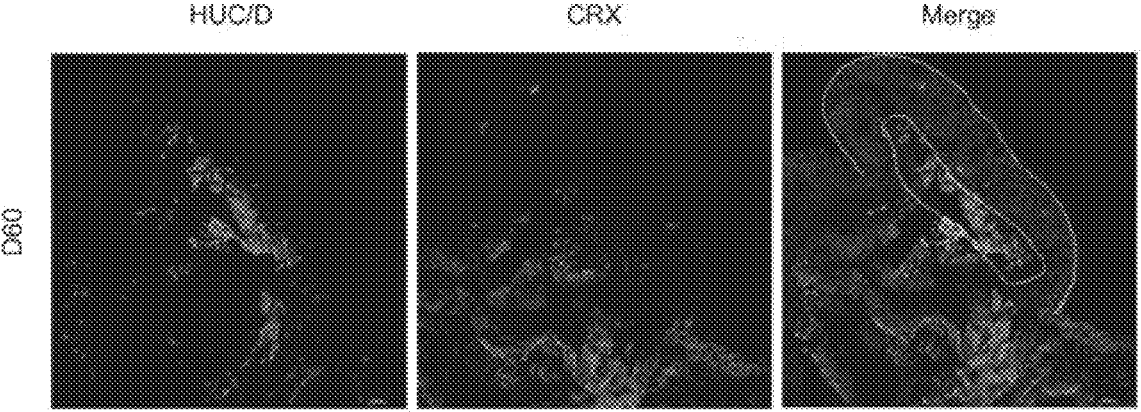
FIG. 3F shows immunofluorescence of cone and rod photoreceptor transcription factors cone-rod homeobox (CRX).
Figure 3G:
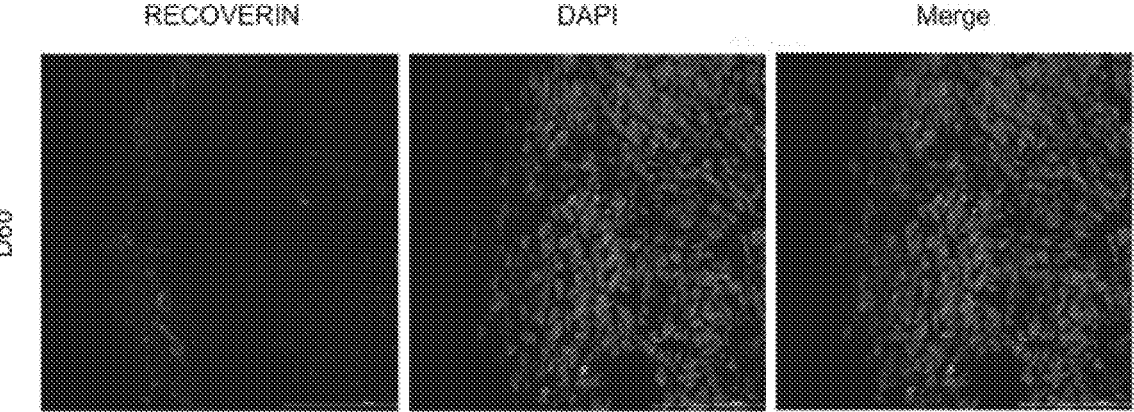
FIG. 3G shows immunofluorescence of recoverin (RECOVERIN).
Figure 3H:
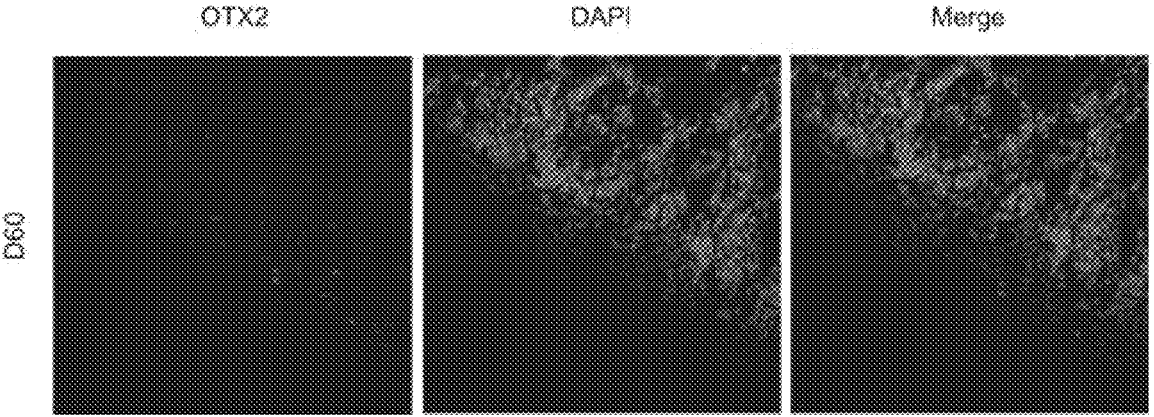
FIG. 3H shows immunofluorescence of photoreceptor transcription factors orthodenticle homeobox 2 (OTX2).

An eye-brain fusion culture method for generating a brain organoid containing optic vesicles based on H9 induction, as shown in FIG. 4, includes the following steps:

step 1, culturing H9 embryonic stem cells to differentiate into a three-dimensional brain organoid containing optic vesicle, including the following steps:

culturing H9 embryonic stem cells in MTESR™ 1 medium (a feeder-free culture and maintenance medium for human embryonic stem cells and induced pluripotent stem cells), followed by cell recovery and ethylene diamine tetraacetic acid (EDTA) digestion, and passaging until the cell confluence reaches 70% after passaging; preparing a single cell suspension using Accutase enzyme to digest the cells in a 37 degrees Celsius (C) incubator for 10 minutes; after cell counting, adding neural induction medium (83% DMEM/F-12, 15% KNOCKOUT™ serum replacement (serum replacement supplement), 1% MEM-NEAA, 1% GLUTAMAX® supplement (L-alanyl-L-glutamine dipeptide supplement), 50 μM β-mercaptoethanol, 10 μM SB431542, 2 μM XAV939, and 10 mM Y27632 (to promote cell aggregation during seeding)); inoculating cells into a ultra-low adhesion V-bottom 96-well plate at a ratio of 100 microliter (μL)/well, with 10,000 cells per well; changing half of the medium with neural induction medium without 10 mM Y27632 (other components unchanged) every day, culturing for 0-5 days, forming neurospheres; transferring the neurospheres to a low-adhesion 3-5 cm culture dish using neurosphere medium (48% DMEM/F-12, 48% NEUROBASAL™ medium (neuronal cell culture medium), 0.4% N2 supplement, 1% B27 supplement without vitamin A, 0.5% MEM-NEAA, 1% GLUTAMAX® supplement (L-alanyl-L-glutamine dipeptide supplement), 1% penicillin/streptomycin, 50 μM β-mercaptoethanol, 2.5 μM SB431542, 1.5 μM BMP-4, and 0.1% MATRIGEL® (extracellular matrix)), and standing for culture; changing half of the medium with the neurosphere medium every day, and culturing until the 6th-7th day; adding optic vesicle brain organoid medium containing retinol acetate (48% DMEM/F-12, 48% NEUROBASAL-™_medium (neuronal cell culture medium), 0.4% N2 supplement, 1% B27 supplement, 100 nMol retinol acetate, 0.5% MEM-NEAA, 1% GLUTAMAX® supplement (L-alanyl-L-glutamine dipeptide supplement), 0.5 μM Dorsomorphin, 1% penicillin-streptomycin, 50 μM β-mercaptoethanol, 2.5 μM SB431542, 0.1% MATRIGEL® (extracellular matrix), and 1.5 μM BMP-4) on the 8th day, adding mature-stage optic vesicle brain organoid medium (48% DMEM/F-12, 48% NEUROBASAL™ medium (neuronal cell culture medium), 0.4% N2 supplement, 1% B27 supplement, 100 nMol retinol acetate, 0.5% MEM-NEAA, 1% GLUTAMAX® supplement (L-alanyl-L-glutamine dipeptide supplement), 0.5 μM Dorsomorphin, 1% penicillin-streptomycin, 50 μM β-mercaptoethanol, 2.5 μM SB431542, 0.1% Ascorbic acid, 10 ng/ml BDNF, and 10 ng/ml CNTF) on the 10th day; transferring to a shaker for long-term rotational culture, and changing half of the medium with mature-stage optic vesicle brain organoid medium every week until a three-dimensional brain organoid containing optic vesicle is differentiated; and step 2: continuing culturing the brain organoid in the step 1, where pigment deposition occurs on one side of the brain organoid from the 20th day to the 30th day, and a strong colored area develops around the 30th day; and obtaining light microscope images of the brain organoid (to observe morphology at different culture stages and pigmented regions); and performing immunostaining and imaging of the brain organoid marked by forebrain pattern and visual field specification, using the marked FOXG1 and SOX2 regions as forebrain region molecules, and RAX and VSX2 regions as the primitive visual field regions (RAX is the retinal and anterior neural fold homeobox transcription factor, VSX2 is the retinal progenitor cell), as well as early retinal development related markers: optic progenitor cells (PAX6), neuronal precursor cells (DCX), amacrine cells (HUC/D), optic ganglion cells (BRN3), retinal epithelial cells (MITF), cone and rod photoreceptor transcription factors (CRX, OTX2), and recoverin (RECOVERIN). As shown in FIG. 1A-FIG. 1B, FIG. 2A-FIG. 2B, FIG. 3A-FIG. 3H, the neural development of the brain organoid containing optic vesicles is in good condition, as well as the development of retina and photoreceptor cells in the brain organoid containing optic vesicles, confirming that the structural function and neural development of the brain organoid containing optic vesicles are in good condition.

The above provides an exemplary description of the present disclosure. It should be noted that any simple modifications, alterations, or equivalent substitutions made without departing from the core of the present disclosure shall fall within the scope of protection of the present disclosure.

What is claimed is:

1. An eye-brain fusion culture method for generating a three-dimensional brain organoid containing optic vesicles through the induction of H9 embryonic stem cells, comprising the following steps:

A) culturing the H9 embryonic stem cells in a feeder-free cell culture and maintenance medium until a cell confluence reaches 70%, B) preparing a single cell suspension, C) removing the feeder-free cell culture and maintenance medium and adding a neural induction medium containing 10 mM Y27632, inoculating in an orifice plate, changing half of the medium with a neural induction medium without 10 mM Y27632 each day for 0-5 days to form neurospheres, wherein the neural induction medium comprises 83% DMEM/F-12, 15% serum replacement supplement, 1% MEM-non-essential amino acids, 1% L-alanyl-L-glutamine dipeptide supplement, 50 μM ß-mercaptoethanol, 10 μM SB431542, and 2 μM XAV939;

D) removing the neural induction medium and adding a neurosphere medium, and changing half of the medium with the neurosphere medium each day until a 6-7$^{th}$ day, wherein the neurosphere medium comprises 48% DMEM/F-12, 48% neuronal cell culture medium, 0.4% N2 supplement, 1% B27 supplement without vitamin A, 0.5% MEM-non-essential amino acids, 1% L-alanyl-L-glutamine dipeptide supplement, 1% penicillin/streptomycin, 50 μM ß-mercaptoethanol, 2.5 M SB431542, 1.5 nM bone morphogenetic protein-4, and 0.1% extracellular matrix;

E) removing the neurosphere medium and adding an early-stage optic vesicle brain organoid medium on an 8th day, wherein the early-stage optic vesicle brain organoid medium comprises 48% DMEM/F-12, 48% neuronal cell culture medium, 0.4% N2 supplement, 1% B27 supplement, 100 nMol retinol acetate, 0.5% MEM-non-essential amino acids, 1% L-alanyl-L-glutamine dipeptide supplement, 0.5 μM Dorsomorphin, 1% penicillin-streptomycin, 50 μM ß-mercaptoethanol, 2.5 μM SB431542, 1.5 nM bone morphogenetic protein-4, and 0.1% extracellular matrix;

F) removing the early-stage optic vesicle brain organoid medium adding a mature-stage optic vesicle brain organoid medium on a 10$^{th}$ day and culturing under rotational culture, and changing half of the medium with the mature-stage optic vesicle brain organoid medium every week until the three-dimensional brain organoid containing the optic vesicles is formed;

wherein the mature-stage optic vesicle brain organoid medium comprises 48% DMEM/F-12, 48% neuronal cell culture medium, 0.4% N2 supplement, 1% B27 supplement, 100 nMol retinol acetate, 0.5% MEM-non-essential amino acids, 1% L-alanyl-L-glutamine dipeptide supplement, 0.5 μM Dorsomorphin, 1% penicillin-streptomycin, 50 μM ß-mercaptoethanol, 2.5 μM SB431542, 0.1% ascorbic acid, 10 ng/ml brain-derived neurotrophic factor, and 10 ng/ml ciliary neurotrophic factor;

G), continuing culture of the brain organoid obtained in step 1 until pigment deposition occurs on one side, and H) performing immunostaining and imaging on the brain organoid marked by a forebrain pattern and a visual field specification to verify a structural function and neural development of the brain organoid.

* * * * *